(12) United States Patent
Li et al.

(10) Patent No.: US 11,154,330 B1
(45) Date of Patent: Oct. 26, 2021

(54) DUAL-TRAJECTORY PEDICLE SCREW SYSTEM FOR IMPROVEMENT OF FIXATION STABILITY

(71) Applicants: Yun-Da Li, Taoyuan (TW); Ching-Lung Tai, Taoyuan (TW); Po-Liang Lai, Taoyuan (TW); Tsung-Ting Tsai, Taoyuan (TW); Ming-Kai Hsieh, Taoyuan (TW); Mu-Yi Liu, Taoyuan (TW)

(72) Inventors: Yun-Da Li, Taoyuan (TW); Ching-Lung Tai, Taoyuan (TW); Po-Liang Lai, Taoyuan (TW); Tsung-Ting Tsai, Taoyuan (TW); Ming-Kai Hsieh, Taoyuan (TW); Mu-Yi Liu, Taoyuan (TW)

(73) Assignee: CHANG GUNG UNIVERSITY, Taoyuan (TW)

( * ) Notice: Subject to any disclaimer, the term of this patent is extended or adjusted under 35 U.S.C. 154(b) by 0 days.

(21) Appl. No.: 17/197,184

(22) Filed: Mar. 10, 2021

(51) Int. Cl.
*A61B 17/70* (2006.01)
(52) U.S. Cl.
CPC .................. *A61B 17/7032* (2013.01)
(58) Field of Classification Search
CPC ...... A61B 17/70; A61B 17/7032–7046; A61B 17/84; A61B 17/844; A61B 17/86; A61B 2017/8655
See application file for complete search history.

(56) References Cited

U.S. PATENT DOCUMENTS

| | | | | |
|---|---|---|---|---|
| 2010/0145397 A1* | 6/2010 | Overes | ................. | A61B 17/725 606/319 |
| 2011/0230920 A1* | 9/2011 | Gorek | ................ | A61B 17/8685 606/305 |
| 2014/0058457 A1* | 2/2014 | Appenzeller | ...... | A61B 17/8685 606/304 |
| 2016/0106477 A1* | 4/2016 | Hynes | ................ | A61B 17/7032 606/279 |
| 2016/0128732 A1* | 5/2016 | Strnad | ................ | A61B 17/7037 606/279 |
| 2017/0020572 A1* | 1/2017 | Hynes | ................ | A61B 17/7032 |

* cited by examiner

*Primary Examiner* — Eduardo C Robert
*Assistant Examiner* — Michelle C Eckman (57) ABSTRACT

A dual-trajectory pedicle screw system includes an internally threaded sleeve and including first part and cylindrical second part, the first part being recessed to form a space, and the second part including projections on top; a main screw including a universal head and a first conic member, the universal head including first and second threaded holes, the first threaded hole being inclined at a first angle, the second threaded hole being inclined at a different second angle, bottom of the universal head being a convex and rotatably disposed in the space; and an auxiliary screw including external threads threadedly secured to the first or second threaded hole so that the auxiliary screw is secured to the main screw at the first or second angle with respect to the main screw, a second conic member extending downward from the external threads, and a fitting member on top of the external threads.

9 Claims, 7 Drawing Sheets

DUAL-TRAJECTORY PEDICLE SCREW SYSTEM FOR IMPROVEMENT OF FIXATION STABILITY

BACKGROUND OF THE INVENTION

1. Field of the Invention

The invention relates to pedicle screws and more particularly to dual-trajectory pedicle screw system for improvement of fixation stability.

2. Description of Related Art

Pedicle screws are widely used in spinal surgery by holding bones in place and have applications including healing degenerative disc disease, spinal fractures, infections and tumors.

There are two typical screws, one is pedicle screw and the other is cortical bone trajectory (CBT) screw available. In use, a pedicle screw is driven from a rear to front, external to internal direction along the spine into the bone. The front end of the pedicle screw enters the medulla of the spine at the end of the procedure. In use, a CBT screw is driven from an internal to external, upward direction along the spine into the bone. The front end of the CBT screw enters the medulla of the spine at the end of the procedure. The initial point of the CBT screw is further inside and downward in comparison with that of the pedicle screw.

Both the pedicle screw and the CBT screw follow a single path in the procedure. The fastening of either screw in the bone of a patient may be loosened or broken due to osteoporosis, failed spinal fusion, spinal fractures, etc. Thus, another surgery is required for the patient. However, another screw cannot be securely fastened in the bone by following the original path. Thus, the screw is required to driven into the bone from another node. This is not desired because it can greatly decrease the structural strength, increase the number of the nodes to be fastened, prolong the surgery time, increase the wound, and greatly lose blood.

Figure 8:
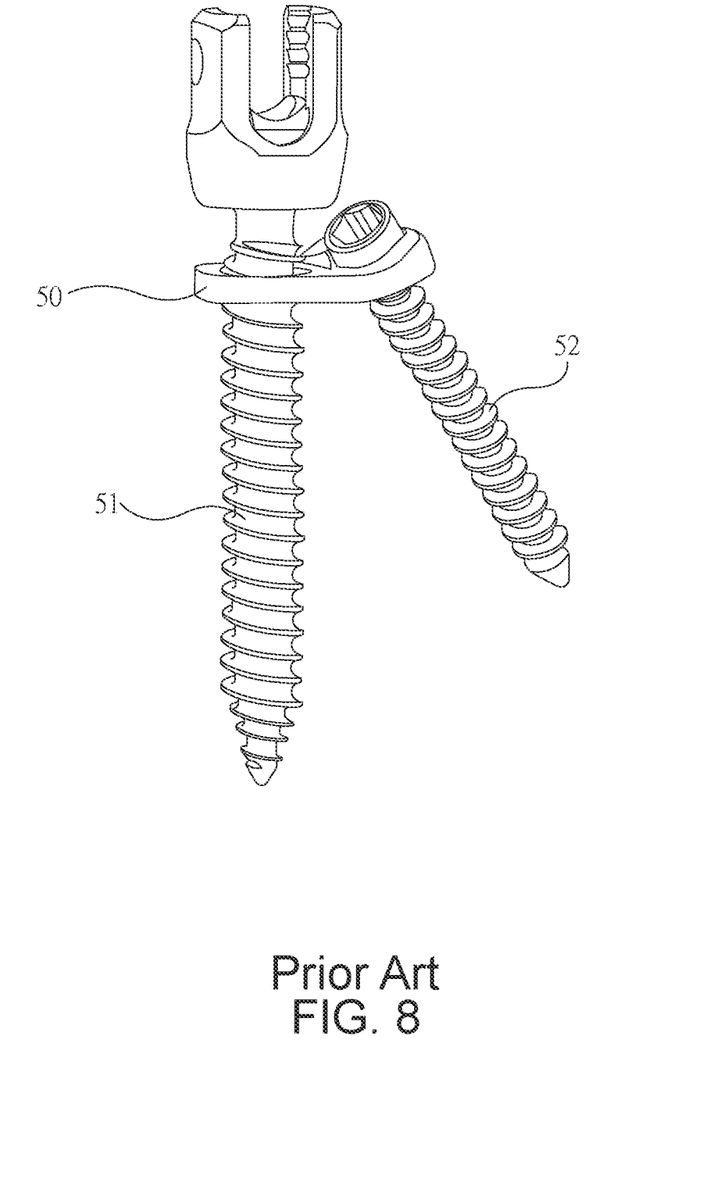
FIG. 8 is a perspective view of a conventional set of pedicle screws.

A set of pedicle screws for sacrum is shown in FIG. 8 and includes a main screw 51, an auxiliary screw 52 and a fastening member 50 for fastening the main screw 51 and the auxiliary screw 52 together. Range of surgery is required to increase for implanting the fastening member 50 in a surgery. However, it may further hurt surrounding tissues and bones. Also, the more components secured together the chance of the components becomes loose increases. Additionally, the main screw 51 is a sacral vertebral arch bone screw and the auxiliary screw 52 is a sacral wing direction bone screw respectively. Their applications are limited to sacrum only.

Thus, the need for improvement still exists.

SUMMARY OF THE INVENTION

The invention has been made in an effort to solve the problems of the conventional art by providing a dual-trajectory pedicle screw system having novel and nonobvious characteristics.

For achieving above and other objects, the invention provides a dual-trajectory pedicle screw system comprising an internally threaded sleeve and including a first part and a second part wherein the first part is recessed to form a space, and the second part is cylindrical and includes a plurality of spaced projections on a top; a main screw including a universal head and a first conic member wherein the universal head includes a first threaded hole and a second threaded hole, the universal head has a flat top, the first threaded hole is inclined at a first angle, the second threaded hole is inclined at a second angle different from the first angle, the universal head has a convex bottom which is rotatably disposed in the space; and an auxiliary screw includes external threads threadedly secured to the first threaded hole or the second threaded hole so that the auxiliary screw is secured to the main screw at the first angle or the second angle with respect to the main screw, a second conic member extending downward from the external threads, and a fitting member formed on a center of a top of the external threads.

In surgery, after the internally threaded sleeve, the main screw and the auxiliary screw have been fastened in the spine, dual pedicle screws are formed. Next, the first U-shaped grooves are put on a cylindrical rod and an externally threaded member is threadedly secured to internal threads, thereby fastening the cylindrical rod. The cylindrical rod can be secured to a plurality of the pedicle screws, thereby increasing the fastening capability of the implanted pedicle screws. A physician may secure the auxiliary screw to the first threaded hole or the second threaded hole based on conditions including position of bones to be healed or osteoporosis of a patient. The dual pedicle screws are more secure in comparison with the single pedicle screw of the conventional art after being implanted and are more effective in preventing the implanted pedicle screw from being loosened or broken.

The invention has the following advantages and benefits in comparison with the conventional art: Increased fastening capability. It is known that a typical pedicle screw is implanted along a single direction. A physician may implant four pedicle screws from two sides of the upper and lower spines. The invention increases the number of the pedicle screws from four to eight, thereby greatly increasing fastening capability. Moreover, the main screw has two threaded holes of different inclined angles. The auxiliary screw can be selectively secured to the first threaded hole or the second threaded hole of the main screw. The universal head of the main screw provides many different orientations for adjusting the direction of the main screw to be implanted into the spine. The dual pedicle screws can greatly increase strength of its interface with the bone, thereby greatly increasing the fastened state of the spine.

Decreased risk of surgery. In comparison with the typical sacral vertebral arch bone screw and the sacral wing direction bone screw, the fastening member is required to fasten the bone screws. To the contrary, the auxiliary screw of the invention is threadedly secured to either threaded hole of the main screw, thereby decreasing the number of components to be fastened, decreasing the possibility of components being loosened, decreasing the range of surgery, decreasing the range of surrounding tissues being hurt, and decreasing the risk of surgery.

Increased convenience. In comparison with the typical sacral vertebral arch bone screw and the sacral wing direction bone screw, the fastening member is disposed in two different styles to fasten two bone screws in consideration of left and right bones of a patient. The fastening members are adapted to the left and right bones of the patient respectively. To the contrary, it is envisaged by the dual-trajectory pedicle screw system of the invention that the auxiliary screw is threadedly secured to either threaded hole of the main screw, thereby eliminating the need of fastening two bone screws by the fastening member. The dual-trajectory pedicle screw system of the invention is adapted to either side of a patient, thereby greatly increasing convenience in surgery.

The above and other objects, features and advantages of the invention will become apparent from the following detailed description taken with the accompanying drawings.

DETAILED DESCRIPTION OF THE INVENTION

Figure 1:
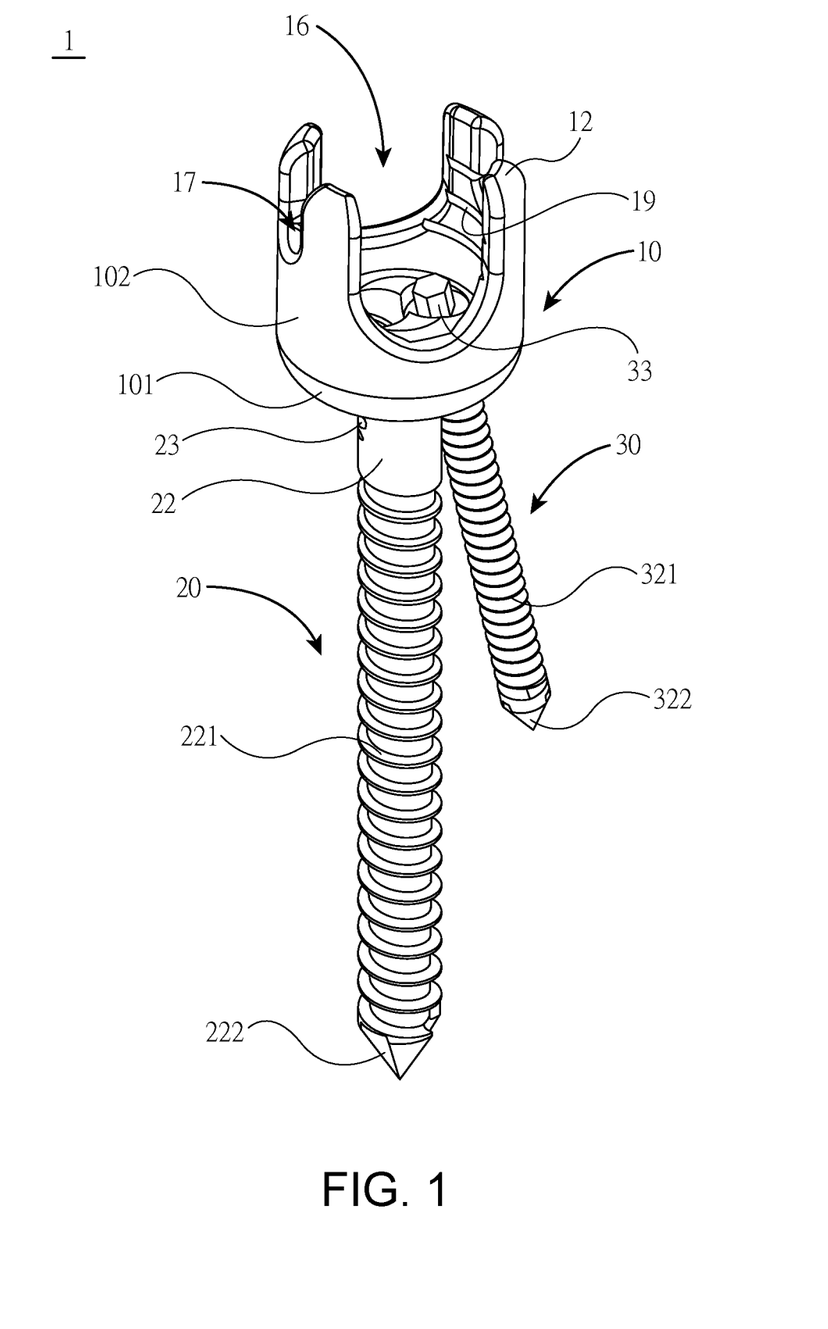
FIG. 1 is a perspective view of a dual-trajectory pedicle screw system according to a first preferred embodiment of the invention.

Referring to FIG. 1, a dual-trajectory pedicle screw system 1 in accordance with a first preferred embodiment of the invention comprises an internally threaded sleeve 10, a main screw 20 and an auxiliary screw 30 as detailed below.

Figure 2:
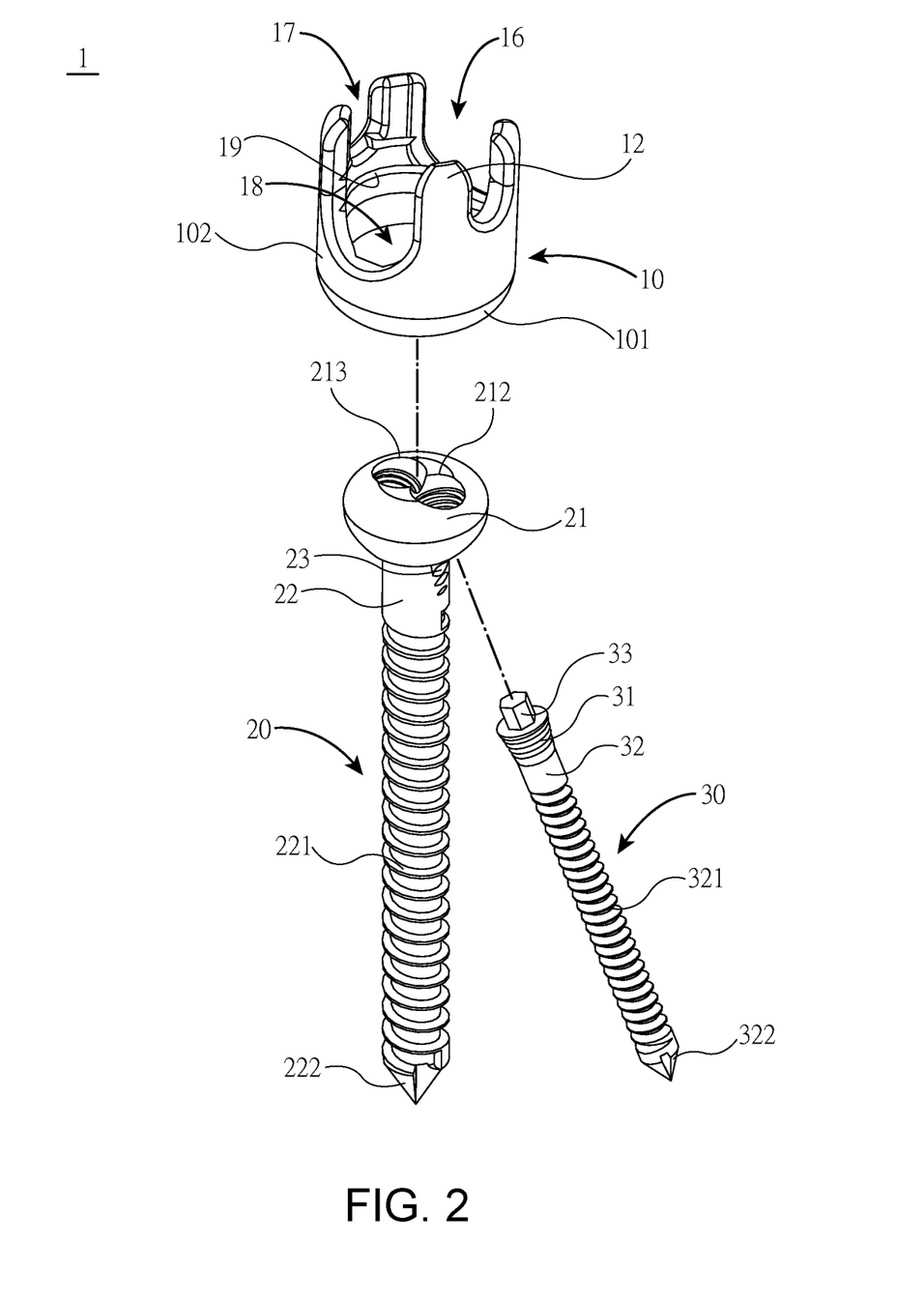
FIG. 2 is an exploded view of FIG. 1.
Figure 5:
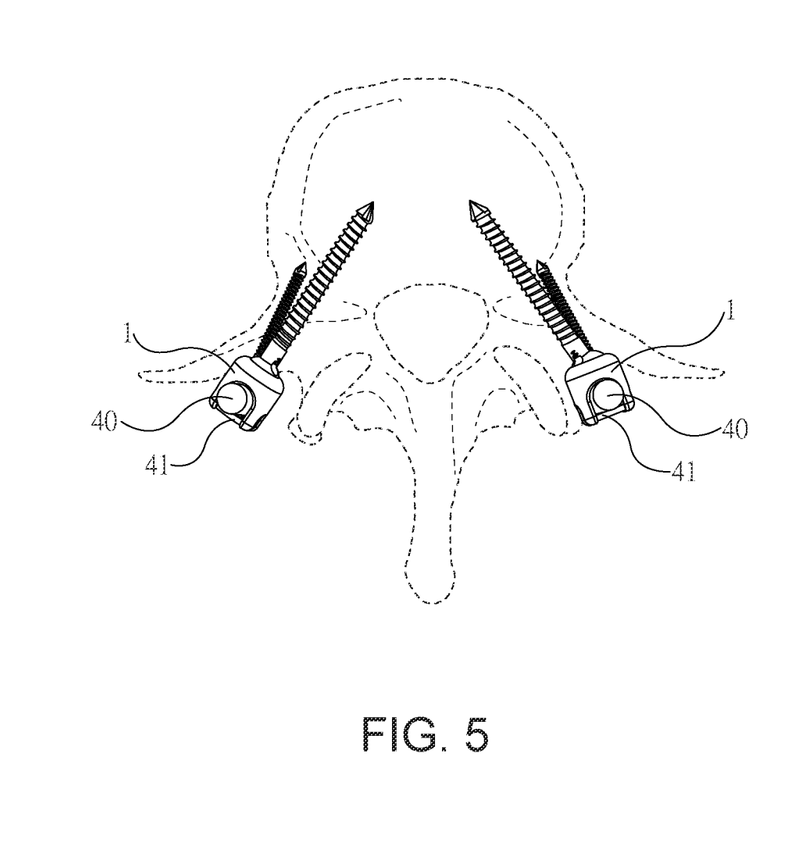
FIG. 5 schematically depicts two dual-trajectory pedicle screw systems of the invention in a first condition of use in surgery.

Referring to FIG. 2 in conjunction with FIG. 5, the internally threaded sleeve 10 includes a first part 101 and a second part 102. The first part 101 is recessed to form a space 18. The second part 102 is cylindrical and includes a plurality of spaced projections 12 on a top, and a plurality of internal threads 19 on inner surfaces of the projections 12. The main screw 20 includes a universal head 21 and a first conic member 22 adjacent the universal head 21. The universal head 21 includes a first threaded hole 212 and a second threaded hole 213. The universal head 21 has a flat top. The first threaded hole 212 is inclined at a first angle and the second threaded hole 213 is inclined at a second angle different from the first angle. The universal head 21 has a convex bottom which is rotatably disposed in the space 18. The first conic member 22 extends downward from the convex bottom of the universal head 21 to form a first threaded section 221 and a first shaped end 222. The auxiliary screw 30 includes external threads 31 threadedly secured to the first threaded hole 212 or the second threaded hole 213, and a second conic member 32 having a second threaded section 321 and a second shaped end 322. A fitting member (e.g., protrusion) 33 is formed on a center of a top of the external threads 31 for securely inserting into a socket of a bone fastening tool, thereby securing the auxiliary screw 30 to the first threaded hole 212 or the second threaded hole 213. Both the first shaped end 222 and the second shaped end 322 are pointed. The main screw 20 includes two sets of a plurality of cavities 23 on a surface connected to the bottom of the universal head 21 and adjacent to the first threaded hole 212 and the second threaded hole 213 respectively. A portion of the second threaded hole 213 is threadedly secured to the cavities 23. In detail, a portion of the second threaded section 321 is threadedly secured to the cavities 23 when the auxiliary screw 30 is threaded secured to the first threaded hole 212 or the second threaded hole 213. This prevents the auxiliary screw 30 from being inclined and increases stability of the auxiliary screw 30 secured to the main screw 20 at an inclined angle with respect to the main screw 20. The number of the projections 19 is four. Two opposite first U-shaped grooves 16 each are formed between two adjacent projections 12 and two opposite second U-shaped grooves 17 each are formed between the other two adjacent projections 12. Each first U-shaped groove 16 is disposed between the second U-shaped grooves 17 and each second U-shaped groove 17 is disposed between the first U-shaped grooves 16. The first U-shaped groove 16 has a depth greater than that of the second U-shaped groove 17. As shown in FIG. 5 specifically, the first U-shaped grooves 16 are put on a cylindrical rod 40 and an externally threaded member 41 is threadedly secured to the internal threads 19, thereby fastening the rod 40. A tool is driven through the hollow of the internally threaded sleeve 10 when the auxiliary screw 30 is threadedly secured to the first threaded hole 212 or the second threaded hole 213. An inclined angle of the first threaded hole 212 is different from that of the second threaded hole 213. Thus, the provision of the two U-shaped grooves 17 increases space for using the tool.

Figure 3:
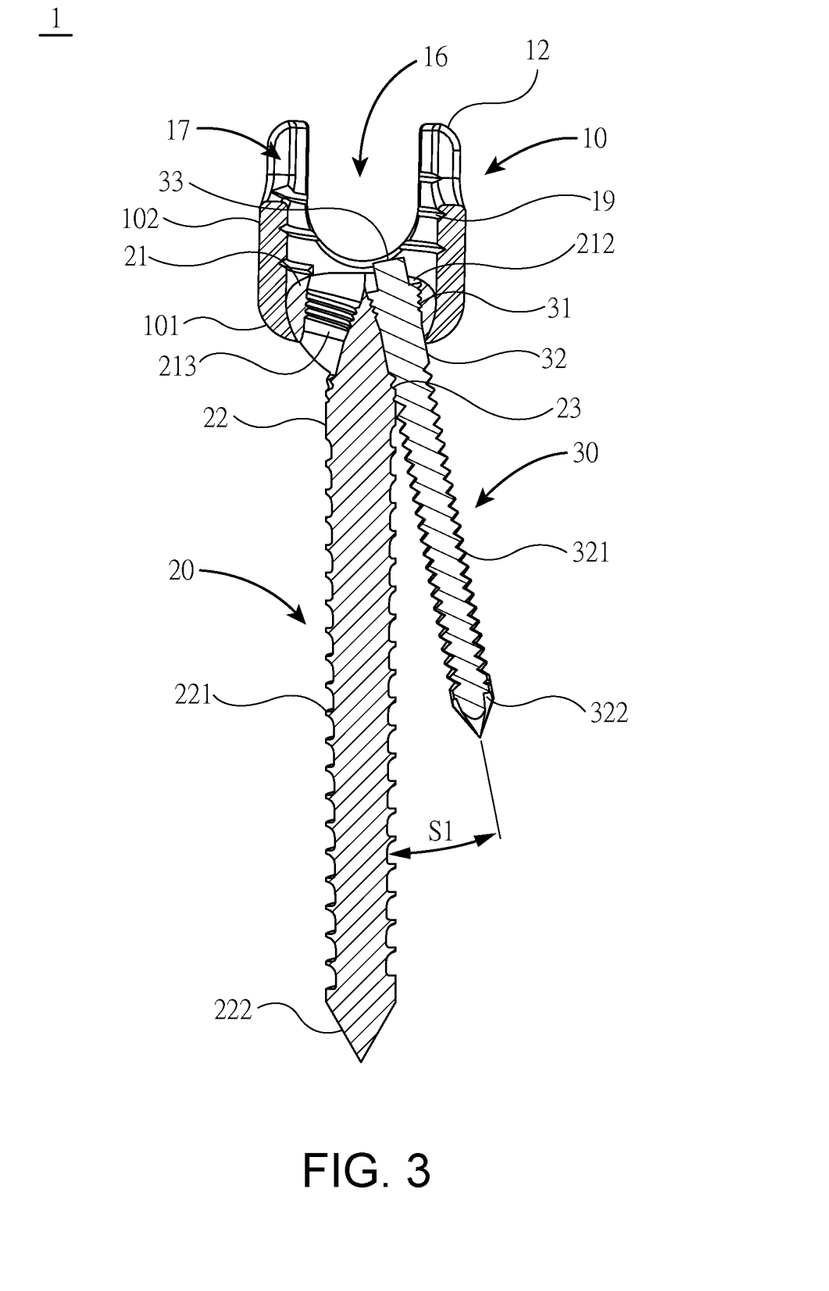
FIG. 3 is a longitudinal sectional view of FIG. 1.

Referring to FIG. 3, the inclined angle of the first threaded hole 212 is different from that of the second threaded hole 213 as shown in the longitudinal sectional view. A physician may secure the auxiliary screw 30 to the first threaded hole 212 or the second threaded hole 213 based on conditions. Thus, its use is more flexible. In the first preferred embodiment, the auxiliary screw 30 is threadedly secured to the first threaded hole 212 and the auxiliary screw 30 is at the first angle S1 with respect to the main screw 20. Preferably, the first angle S1 is 10 degrees.

Figure 4:
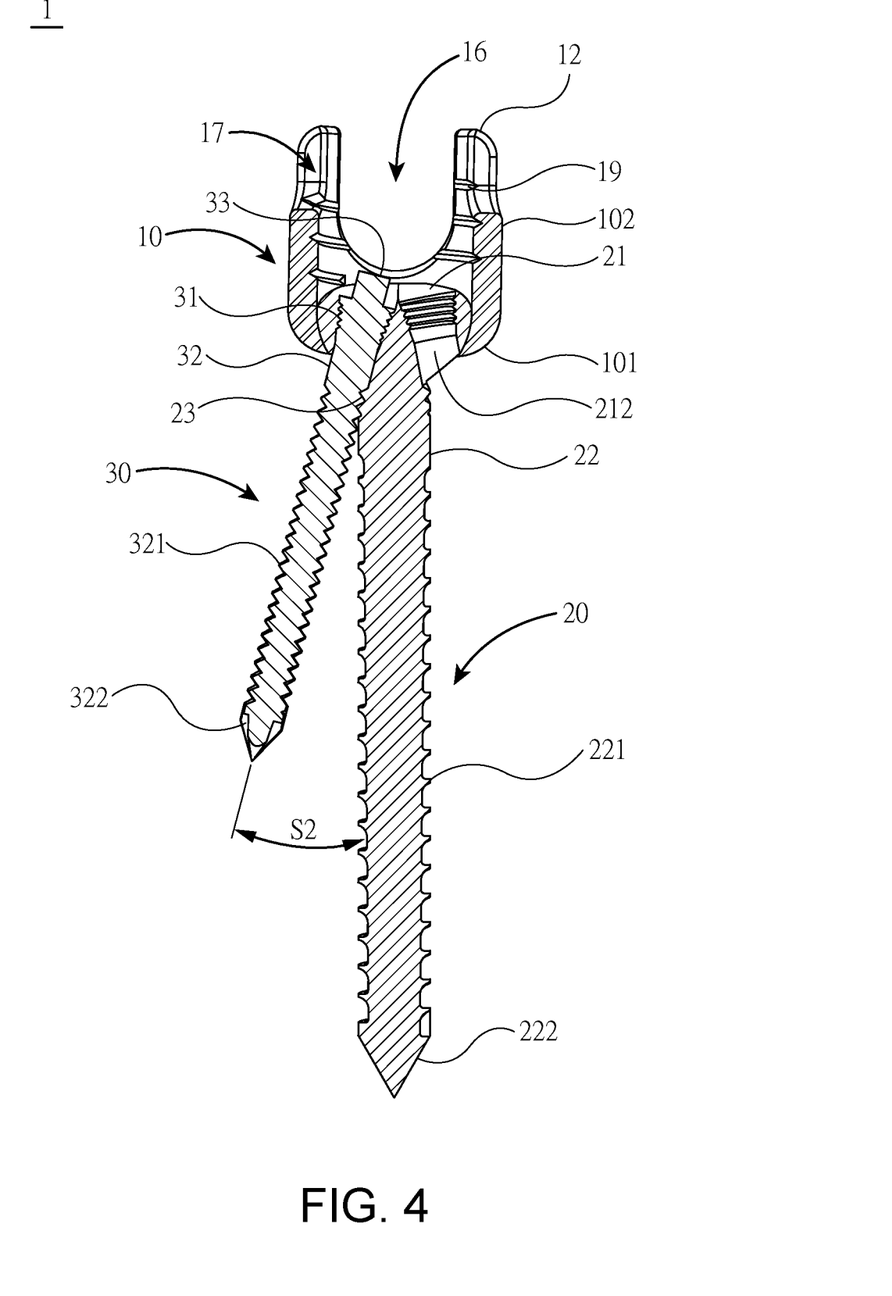
FIG. 4 is a longitudinal sectional view of the dual-trajectory pedicle screw system according to a second preferred embodiment of the invention.

Referring to FIG. 4, the dual-trajectory pedicle screw system 1 in accordance with a second preferred embodiment of the invention is shown. The characteristics of the second preferred embodiment are substantially the same as that of the first preferred embodiment except the following: the auxiliary screw 30 is threadedly secured to the second threaded hole 213 and the auxiliary screw 30 is at the second angle S2 with respect to the main screw 20. Preferably, the second angle S2 is 15 degrees.

It is envisaged by the invention that the auxiliary screw 30 can be secured to the main screw 20 at one of a plurality of different angles with respect to the main screw 20; and the universal head 21 of the main screw 20 provides many different orientations. In surgery, a physician may secure the auxiliary screw 30 to the first threaded hole 212 or the second threaded hole 213 based on conditions including position of bones to be healed or osteoporosis of a patient. As a result, the dual-trajectory pedicle screw system 1 has increased fastening capability.

Figure 6:
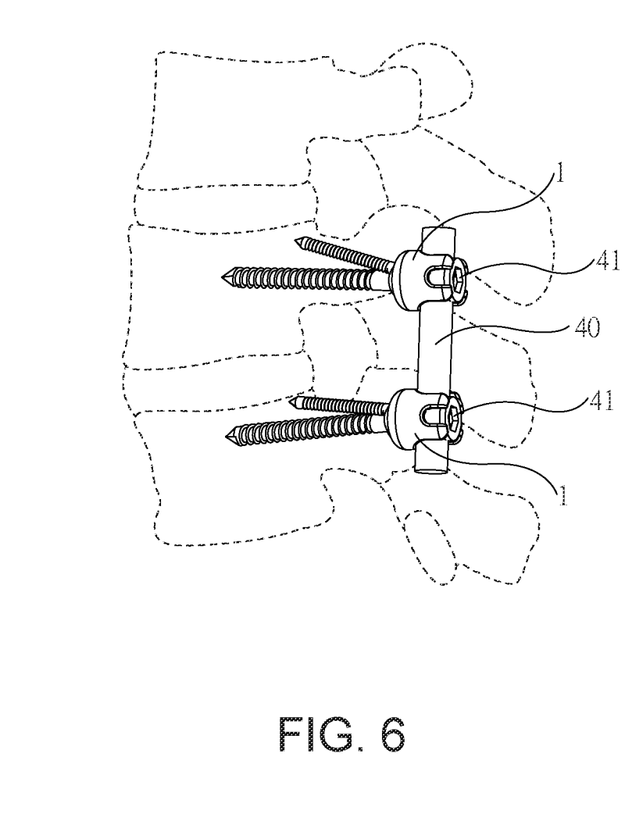
FIG. 6 schematically depicts the dual-trajectory pedicle screw systems of FIG. 5 from another angle of view.
Figure 7:
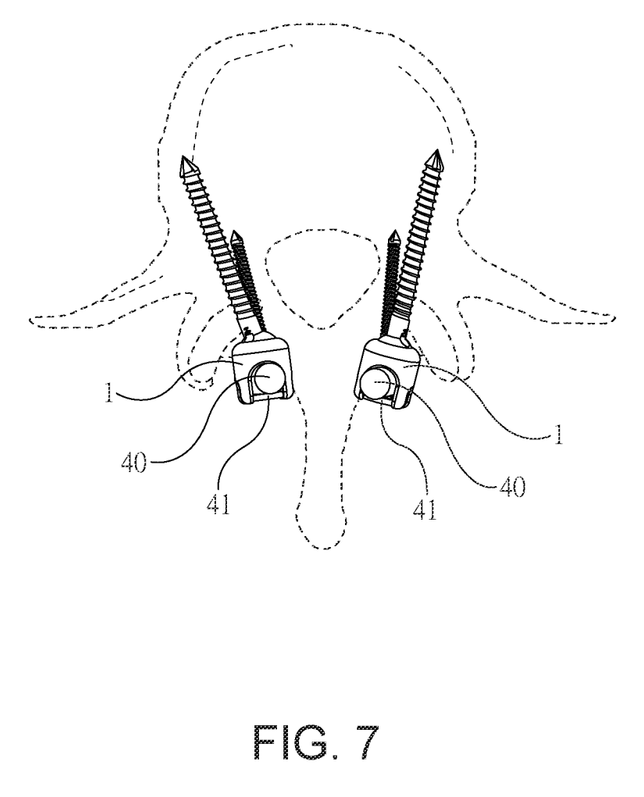
FIG. 7 schematically depicts the dual-trajectory pedicle screw systems of the invention in a second condition of use in surgery.

Referring to FIGS. 5, 6 and 7 in conjunction with FIG. 2, two different conditions of use in surgery are illustrated. After the dual-trajectory pedicle screw system 1 has been driven in the bones, the cylindrical rod 40 is disposed in the first U-shaped grooves 16, and the externally threaded member 41 is threadedly secured to the internal threads 19, thereby fastening the cylindrical rod 40. The cylindrical rod 40 can be disposed across the two dual-trajectory pedicle screw systems 1 to further increase the fastening capability.

The dual-trajectory pedicle screw system 1 of the invention has the following advantages and benefits in comparison with the conventional art: Increased fastening capability. Decreased number of nodes to be fastened in a first or another surgery. Decreased wound. Decreased surgery time. Decreased blood loss. Wide applications. In addition to surgery of anterior spine or posterior spine, the dual-trajectory pedicle screw system 1 of the invention can be applied to surgery of thoracic spine, lumbar spine, or sacral spine with both surgery risk and surgery expenditure decreased to a maximum.

While the invention has been described in terms of preferred embodiments, those skilled in the art will recognize that the invention can be practiced with modifications within the spirit and scope of the appended claims.

What is claimed is:

1. A dual-trajectory pedicle screw system, comprising:
    an internally threaded sleeve and including a first part and a second part wherein the first part is recessed to form a space, and the second part is cylindrical and includes a plurality of spaced projections on a top;
    a main screw including a universal head and a first conic member wherein the universal head includes a first threaded hole and a second threaded hole, the universal head has a flat top, the first threaded hole is inclined at a first angle, the second threaded hole is inclined at a second angle different from the first angle, the universal head has a convex bottom which is rotatably disposed in the space; and
    an auxiliary screw includes, from top to bottom, external threads threadedly secured to the first threaded hole or the second threaded hole so that the auxiliary screw is secured to the main screw at the first angle or the second angle with respect to the main screw, a second conic member extending downward from the external threads, and a fitting member formed on a center of a top of the external threads.

2. The dual-trajectory pedicle screw system of claim 1, wherein the first angle is 10 degrees.

3. The dual-trajectory pedicle screw system of claim 1, wherein the second angle is 15 degrees.

4. The dual-trajectory pedicle screw system of claim 1, further comprising a plurality of internal threads on inner surfaces of the projections, two opposite first U-shaped grooves each formed between two adjacent ones of the projections, a rod with the first U-shaped grooves disposed therein, and an externally threaded member threadedly secured to the internal threads, thereby fastening the rod.

5. The dual-trajectory pedicle screw system of claim 4, further comprising two opposite second U-shaped grooves each formed between the other two adjacent ones of the projections, each first U-shaped groove being disposed between the second U-shaped grooves, each second U-shaped groove being disposed between the first U-shaped grooves, and the first U-shaped groove having a depth greater than that of the second U-shaped groove.

6. The dual-trajectory pedicle screw system of claim 1, wherein the first conic member includes a first threaded section and a first shaped end, and the second conic member includes a second threaded section and a second shaped end.

7. The dual-trajectory pedicle screw system of claim 6, wherein both the first shaped end and the second shaped end are pointed.

8. The dual-trajectory pedicle screw system of claim 1, wherein the main screw further comprises two sets of at least one cavity on a surface connected to the bottom of the universal head and adjacent to the first threaded hole and the second threaded hole respectively; and wherein a portion of the second threaded section is threadedly secured to the at least one cavity.

9. The dual-trajectory pedicle screw system of claim 1, wherein the fitting member is a protrusion.

\* \* \* \* \*